United States Patent
Bal et al.

(10) Patent No.: US 8,772,552 B2
(45) Date of Patent: Jul. 8, 2014

(54) PROCESS FOR THE SELECTIVE HYDROXYLATION OF BENZENE WITH MOLECULAR OXYGEN

(71) Applicant: Council of Scientific & Industrial Research, New Delhi (IN)

(72) Inventors: Rajaram Bal, Dehradun (IN); Shubhra Acharyya Shankha, Dehradun (IN); Shilpi Ghosh, Dehradun (IN); Bipul Sarkar, Dehradun (IN); Karan Singh Rawat, Dehradun (IN); Chandrashekar Pendem, Dehradun (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/623,653

(22) Filed: Sep. 20, 2012

(65) Prior Publication Data

US 2013/0096351 A1    Apr. 18, 2013

(30) Foreign Application Priority Data

Sep. 22, 2011  (IN) .............................. 2765/DEL/2011

(51) Int. Cl.
*C07C 37/58* (2006.01)
*B01J 23/00* (2006.01)

(52) U.S. Cl.
USPC ........................... 568/802; 502/317; 502/305

(58) Field of Classification Search
USPC ................................... 568/802; 502/317, 305
See application file for complete search history.

(56) References Cited

FOREIGN PATENT DOCUMENTS

JP        2011-207688      *   9/2010   ............... B01J 29/48

OTHER PUBLICATIONS

Shu-Ichi Niwa, et al.; One-Step Conversion of Benzene to Phenol with a Palladium Membrane; www.sciencemag.org, Science, Jan. 4, 2002, pp. 105-107; vol. 295.

Min Jian, et al.; Sodium Metavanadate Catalyzed Direct Hydroxylation of Benzene to Phenol with Hydrogen Peroxide in Acetonitrile Medium; Journal of Molecular Catalysis; Chemical 253 (2006) pp. 1-7.

Rajaram Bal, et al.; Direct Phenol Synthesis by Selective Oxidation of Benzene with Molecular Oxygen on an Interstitial-N/Re Cluster/Zeolite Catalyst; Agnew. Chem. Int. Ed.; 2006; pp. 448-452; vol. 45.

Xiaohan Gao, et al.; A New Application of Clay-Supported Vanadium Oxide Catalyst to Selective Hydroxylation of Benzene to Phenol; Applied Clay Science; 2006; pp. 1-6; vol. 33.

Yu-Wen Chen, et al.; Characteristics of V-MCM-41 and it's Catalytic Properties in Oxidation of Benzene; Ind. Eng. Chem. Res.; 1999; pp. 1893-1903; vol. 38.

Masakazu Iwamoto, et al.; Catalytic Oxidation by Oxide Radical Ions. 1. One-Step Hydroxylation of Benzene to Phenol over Group 5 and 6 Oxides Supported on Sillica Gel; Journal of Physical Chemistry; Mar. 17, 1983; pp. 903-904; vol. 87; No. 6.

Roger A Sheldon; Catalysis and Pollution Prevention; Chemistry & Industry; Jan. 6, 1997; p. 13.

T. Tatsumi, et al.; Hydroxylation of Benzene and Hexane by oxygen and Hydrogen over Palladium-Containing Titanium Silicalites; Department of Synthetic Chemistry, Faculty of Engineering, The University of Tokyo, Hongo, Tokyo; 1992; pp. 1446-1447.

* cited by examiner

*Primary Examiner* — Johann R Richter
*Assistant Examiner* — Mark Luderer
(74) *Attorney, Agent, or Firm* — Blank Rome LLP

(57) ABSTRACT

The present invention provides an improved process for the selective hydroxylation of benzene. The process provides a direct single step selective vapor phase hydroxylation of benzene to phenol using molecular oxygen (air) over Cu—Cr oxide catalysts. The process provides benzene conversion of 10 to 45% and selectivity for phenol up to 100%.

9 Claims, No Drawings

PROCESS FOR THE SELECTIVE HYDROXYLATION OF BENZENE WITH MOLECULAR OXYGEN

FIELD OF INVENTION

The present invention relates to an improved process for the selective hydroxylation of benzene with molecular oxygen (air) over solid catalysts. More particularly, the present invention relates to an improved process for the vapour phase selective hydroxylation of benzene to phenol by using molecular oxygen (air) over Cu—Cr oxide.

BACKGROUND OF THE INVENTION

Phenol is a very important chemical for the chemical industry due to its widespread use in the fields of resin, plastics, pharmaceuticals, agrochemicals, etc. It is mainly used for the production of a large no of intermediates such as bisphenol, caprolactum, aniline, alkylphenol, chlorophenol, salicylic acid, etc., which are then further used to produce epoxy resin for paints, polycarbonate plastics for CDs and domestic appliances, nylon, polyamides, antioxidants, surfactants, detergents, anticeptics, medicines etc. At present phenol is mainly produced by three steps Cumene Process. However, the process has several disadvantages such as poor ecology, formation of an explosive intermediates (cumene hydroperoxide), multistep character which makes it difficult to achieve high phenol yield w.r.t. benzene. The main concern in the fine chemical and drug intermediates are the amount of waste generated per unit weight of desired product (called E-factor by R A Sheldon in Chemsitry & Industry, 6 Jan. 1997, P 13) and poor atom efficiencies (kg of product produced per Kg of reactants used) due to the use of stoichiometric reagents and minerals acid/base catalysts. In this context, the use of solid catalysts which are eco-safe and reusuable become important. Moreover a major problem with this process is that it produces phenol is driving its price down and also hurting the economics of phenol as well. This concern is the impetus for researchers to develop a direct single step co-product free and environment friendly route to phenol.

There are reports on the production of phenol by direct hydroxylation of benzene with different oxidants over different solid catalyst but to the best of our knowledge there is no reference for the use of molecular oxygen (air) only for this purpose.

Reference may be made to article in the Journal of Physical Chemistry, 1983, 87, 903-905, in which Japanese workers reported the use of nitrous oxide for the hydroxylation of benzene to phenol—using vanadium pentaoxide/silica catalyst at 550° C. to achieve 10% benzene conversion and 70% phenol selectivity.

Reference may also be made to patents WO9527691, 1995 and WO9527560, 1995 wherein Panov et al developed a one step process for the manufacture of phenol from benzene using nitrous oxide as the and ZSM-5 and ZSM-11 as the catalysts. The drawbacks of this process are deactivation of catalyst, loss of selectivity of catalyst and side reaction (combustion of benzene by nitrous oxide). It is economically attractive only if $N_2O$ is available as the by product of some other process such as the two step oxidation of cyclohexane to adipic acid.

Reference may be made to article in J. Chem. Soc. Chem. Com., 1992, 1446-1447 wherein Tatsumi et al. describe a process for the preparation of phenol from benzene with $H_2$ and $O_2$ which uses a catalyst consisting of palladium supported on TS-1. Operating according to this process, a conversion of benzene of 0.07% is obtained with a turnover of Palladium of 13.5.

Another reference may be made to European patent EP0894783, 1998, wherein a process for the synthesis of phenol by catalytic oxidation of benzene in the presence of titanium silicate and by $H_2O_2$ prepared in situ by reaction of oxygen carbon monoxide and water in the presence of catalytic complexes consisting of palladium with a nitrogenated ligand and a non-coordinating counter ion. The selectivity of benzene to phenol is greater than 95%, but benzene conversions were only 1-2%.

Reference may be made to the article in Journal of Molecular CatalysisA: Chemical 2006, 253, 1-7, wherein phenol is prepared by homogeneous liquid phase direct catalytic oxidation of benzene at room temperature in acetonitrile solvent using sodium metavenadate as the catalyst and hydrogen peroxide as the oxidant. Phenol yield of 13.5% with a selectivity of 94% was reported.

Reference may be made to Ind. Eng. Chem. Res. 1999, 38, 1893-1903, wherein phenol was synthesized by direct liquid phase benzene hydroxylation by $H_2O_2$ using V-MCM-41 as the catalyst under mild conditions. Operating accordingly to this process, a conversion of benzene of 13% and selectivity for phenol of 48% was obtained.

Another reference may be made to Science 2002, 105, 295, wherein phenol was obtained by direct vapour phase hydroxylation of benzene using Pd-membrane as a catalyst using $O_2$ and $H_2$ as the oxidant. Phenol yield of 12% and selectivity of 80-97% was obtained.

Another reference may be made to article in Applied Clay Science 2006, 33, 1-6, wherein selective direct hydroxylation of benzene with hydrogenperoxide to phenol was carried out on a clay-supported vanadium oxide catalyst. Under mild reaction conditions at 60° C., high selectivity to phenol of 94% was obtained but conversion of benzene was only 14%.

Another reference may be made to article Angew. Chem. Int. Ed. 2006, 45, 448, wherein phenol was obtained by direct vapour phase hydroxylation of benzene using Re cluster/zeolite as a catalyst using $O_2$ and $NH_3$ as the oxidant. Phenol yield of 5% and selectivity of 80-97% was obtained.

The drawback of the processes reported so far is that they do not exhibit sufficiently high conversions of benzene for high selectivity of phenol to be of interest for industrial application. In most of the cases hazardous oxidizing agent $N_2O$, $H_2O_2$ or expensive $H_2$ with $O_2$ or reducing agent $NH_3$ with $O_2$ was used and also lots of unnecessary by-products was formed. In addition, the catalysts used have a limited activity under the operating conditions. There is, therefore, an evident necessity for further improvements in the process for the selective conversion of benzene to phenol.

OBJECTIVES OF THE INVENTION

The main object of the present invention is to provide an improved process for the selective hydroxylation of benzene with molecular oxygen (air) over solid catalysts which obviates the drawbacks of hitherto known methods as detailed above.

Another object of the present invention is to provide an improved process for the selective hydroxylation of benzene with molecular oxygen (air) as the oxidant and Cu—Cr oxide as the catalyst.

Still another object of the present invention is to provide an improved process, which gives phenol from benzene with high selectivity.

Yet another object of the present invention is to provide a process which uses environmental friendly green oxidizing agent, air for the synthesis of phenol.

Yet another object of the present invention is to provide a process which works under continuous process for the synthesis of phenol.

Yet another object of the present invention is to provide a process which works under mild conditions for the synthesis of phenol.

SUMMARY OF THE INVENTION

Accordingly, the present invention provides an improved process for the selective hydroxylation of benzene with molecular oxygen (air) over solid catalysts which comprises reacting benzene with air in the pressure range of 1-5 MPa, at a temperature of 150-450° C. with a liquid hourly space velocity (LHSV, benzene feed/g catalyst/hour) in the range of 20 to 400 for a period of 1-30 hrs in the presence of Cu—Cr oxide catalyst to obtain phenol.

In an embodiment of the invention, the molar ratio of Cu to Cr of the catalyst varied in the range of 0.1 to 0.5.

In one embodiment of the invention, the air pressure is preferably in the range of 2-5 MPa.

In another embodiment of the invention, the reaction temperature is preferably in the range 200-400° C.

In yet another embodiment, the liquid hourly space velocity (LHSV) is preferably in the range 30 to 300.

In still another embodiment, the reaction time used is preferably in the range 2-30 h.

In still another embodiment, the conversion of benzene is in the range of 1-42%.

In still another embodiment, the selectivity of the phenol obtained in the range of 50-100%.

In still another embodiment, yield of phenol is in the range of 2-30%.

DETAILED DESCRIPTION OF THE INVENTION

The present invention provides an improved process for the production of phenol by vapour phase selective hydroxylation of benzene using air as the oxidant and Cu—Cr oxide as the catalyst which involves the following steps
1. Synthesis of Cu—Cr oxide using the gel composition of $Cu(NO_3)_2$, $Cr(NO_3)_3$, cetyltrimethylammonium bromide, hydrazine, in the molar ratio of Cu: CTAB: Hydrazine: $H_2O$=1:0.75:1:300
  40 g $Cr(NO_3)_3.9H_2O$ was dissolved in 40 g water and 2.95 g $Cu(NO_3)_2.3H_2O$ was added to it. Into this solution, 3.9 g cetyltrimethylammonium bromide dissolved with 5 g $H_2O$ was added dropwise to get a homogeneous mixture. Then 0.5 g hydrazine dissolved with 2 g water was added dropwise to this mixture. The gel formed was stirred for 3 h and finally the mixture was hydrothermally treated at 140-170° C. for 20-24 h in a Teflon lined stainless steel autoclave under a autogeneous pressure. The product was washed with excess distilled water and ethanol and dried at ambient temperature for 6 -10 h and calcined in the temperature between 300 to 550° C. in air.
2. The molar ratio of Cu to Cr varied in the range between 0.1 to 0.7
3. Calcination of the materials at 300-750° C. for 4-8 h
4. Benzene hydroxylation was carried out in a fixed bed down-flow reactor using benzene and air as feeds for 1 to 30 h to get phenol.

The air pressure is preferably in the range 2 to 5 MPa

The reaction temperature is preferably in the range 200-400° C.

The liquid hourly space velocity (LHSV) is preferably in the range 30 to 300

The benzene conversion is obtained 10-30 wt % and selectivity to phenol approaching 100%.

The detailed steps of the process are:

The reaction was carried out in a fixed bed down flow high pressure reactor by charging 0.2 g catalyst. The pressure of the reactor was maintained by using air.

Benzene was introduced in the reactor by using a HPLC pump. The reaction mixtures were analyzed by two online GCs with an FID detector by using capillary column for hydrocarbons and a TCD detector by using a Porapack-Q column for inorganic materials online GC The following examples are given by way of illustration of working of the invention in actual practice and should not be constructed to limit the scope of the present invention in any way.

EXAMPLE—1

This example describes the hydroxylation of benzene by vapour phase reaction in air using Cu—Cr oxide as the catalyst.

Process Conditions
Catalyst: 0.2 g
Cu:Cr molar ratio in the catalyst=1:2.5
Air pressure : 4 Mpa
Benzene flow=0.1 ml/min (LHSV=30)
Temperature: 350° C.
Reaction time: 6 h
Product Analysis:
Benzene conversion: 28.9%
Selectivity of phenol : 95.2%

EXAMPLE—2

The example describes the effect of temperature on yield and selectivity of phenol. The product analysis presented in Table—1.
Process Conditions:
Catalyst: 0.2 g
Cu:Cr molar ratio in the catalyst=1:2.5
Air pressure : 4 Mpa
Benzene flow=0.1 ml/min
Reaction time: 6 h

TABLE 1

Effect of temperature on benzene conversion, phenol yield and selectivity

| Temperature | Benzene Conversion | Phenol | |
|---|---|---|---|
| (° C.) | (%) | Yield | Selectivity |
| 200 | 2.4 | 2.4 | 100 |
| 250 | 7.5 | 7.4 | 98.4 |
| 300 | 17.4 | 16.9 | 97.2 |
| 350 | 28.9 | 27.5 | 95.2 |
| 400 | 41.7 | 21.1 | 50.7 |

EXAMPLE—3

The example describes the effect of time on stream on yield and selectivity of phenol. The product analysis presented in Table 2

Process Conditions:
Catalyst: 0.2 g
Cu:Cr molar ratio in the catalyst=1:2.5
Air pressure : 4 Mpa
Benzene flow=0.1 ml/min
Reaction temperature : 350° C.

TABLE 2

Effect of time on stream on benzene conversion, phenol yield and selectivity

| Time on stream | Benzene Conversion | Phenol | |
|---|---|---|---|
| (h) | (%) | Yield | Selectivity |
| 2 | 28.2 | 27.5 | 95.2 |
| 6 | 28.9 | 27.5 | 95.1 |
| 12 | 29.4 | 28.1 | 95.6 |
| 18 | 28.5 | 27.4 | 96 |
| 28 | 27.9 | 26.5 | 94.9 |

EXAMPLE—4

The example describes the effect of air pressure on yield and selectivity of phenol. The product analysis presented in Table—3.
Process Conditions:
Catalyst: 0.2 g
Cu:Cr molar ratio in the catalyst=1:2.5
Reaction temperature : 350° C.
Benzene flow=0.1 ml/min
Reaction time: 6 h

TABLE 3

Effect of air pressure on benzene conversion, phenol yield and selectivity

| Reaction Pressure | Benzene Conversion | Phenol | |
|---|---|---|---|
| (MPa) | (%) | Yield | Selectivity |
| 2 | 2.5 | 2.1 | 97.1 |
| 3 | 17.4 | 16.7 | 95.8 |
| 4 | 28.9 | 27.5 | 95.1 |
| 5 | 31.3 | 24.9 | 79.5 |

EXAMPLE—5

The example describes the effect of liquid hourly space velocity on yield and selectivity of phenol. The product analysis presented in Table—4.
Process Conditions:
Catalyst: 0.2 g
Cu:Cr molar ratio in the catalyst=1:2.5
Reaction temperature : 350° C.
Air pressure: 4 MPa
Reaction time: 6 h

TABLE 4

Effect of liquid hourly space velocity (LHSV) on benzene conversion, phenol yield and selectivity

| LHSV | Benzene | Phenol | |
|---|---|---|---|
| (ml benzene/h/$g_{cat}$) | Conversion (%) | Yield | Selectivity |
| 30 | 28.9 | 27.5 | 95.1 |
| 60 | 20.1 | 19.3 | 96.2 |
| 100 | 12.5 | 12.1 | 96.7 |
| 300 | 4.6 | 4.5 | 97.1 |

The main advantages of the present invention are:
1. The process of the present invention converts benzene to phenol in a single step with a single catalyst.
2. The process provides not only good conversion but also good selectivity for phenol.
3. The oxidizing agent, air, used in this process has the major advantages of this process.
4. The process does not produce any by-products is also a major advantage of this process.
5. The process does not need any addition reagent to generate active oxygen.
6. The catalyst is used in very low amounts.
7. The catalyst does not deactivate till 30 h with the reaction stream.

We claim:
1. A process for making phenol comprising the step of selectively hydroxylating benzene with molecular oxygen over solid catalysts which comprises reacting benzene with air in the pressure range of 1-5 MPa, at a temperature of 150-450° C. with a liquid hourly space velocity (LHSV, benzene feed/g catalyst/hour) in the range of 20 to 400 for a period of 1-30 hrs to obtain phenol, wherein the solid catalyst is Cu—Cr oxide.
2. A process as claimed in claim 1, wherein the molar ratio of Cu to Cr of the catalyst varied in the range of 0.1 to 0.5.
3. A process as claimed in claim 1, wherein the air pressure is in the range of 2-5 MPa.
4. A process according to claim 1, wherein the reaction temperature is in the range 200-400° C.
5. A process as claimed in claim 1, wherein the liquid hourly space velocity (LHSV) is in the range 30 to 300.
6. A process as claimed in claim 1, wherein the reaction time used is in the range 2-30 h.
7. A process as claimed in claim 1, wherein the conversion of benzene is in the range of 1-42%.
8. A process as claimed in claim 1, wherein the selectivity of the phenol obtained in the range of 50-100%.
9. A process as claimed in claim 1, wherein the molecular oxygen is provided from air.

* * * * *